United States Patent [19]

Leach et al.

[11] Patent Number: 4,622,248

[45] Date of Patent: Nov. 11, 1986

[54] PRESERVATIVE COMPOSITION FOR WOOD

[75] Inventors: Robert M. Leach, Grand Island; Richard J. Ziobro, Buffalo, both of N.Y.

[73] Assignee: Osmose Wood Preserving Co. of America, Inc., Buffalo, N.Y.

[21] Appl. No.: 736,783

[22] Filed: May 22, 1985

Related U.S. Application Data

[63] Continuation-in-part of Ser. No. 596,637, Apr. 4, 1984, abandoned.

[51] Int. Cl.$^4$ ............................................. C09D 5/16
[52] U.S. Cl. ............................... 427/440; 106/18.32; 106/18.36; 424/141; 424/145; 424/161; 424/166; 514/494; 514/499; 514/501; 514/505
[58] Field of Search ............. 106/18.36, 18.32; 424/141, 145, 161, 166; 427/440; 514/494, 499, 501, 505

[56] References Cited

U.S. PATENT DOCUMENTS

| | | | |
|---|---|---|---|
| 3,094,459 | 6/1963 | Pickren | 424/141 |
| 4,001,400 | 1/1977 | Hager | 424/294 |
| 4,325,939 | 4/1982 | Shah | 424/49 |

*Primary Examiner*—Lorenzo B. Hayes
*Attorney, Agent, or Firm*—Christel, Bean & Linihan

[57] ABSTRACT

The present invention provides a method and composition for preserving wood and other cellulose based materials against destructive organisms responsible for rot and decay, namely fungus and insects. The composition comprises an aqueous ammoniacal solution of a preservative metal compound and an organic acid selected from the group consisting of aliphatic dicarboxylic acids containing 2–10 carbon atoms per molecule, aliphatic mono, di or tricarboxylic hydroxy acids containing 2–6 carbon atoms per molecule or a mixture of these acids and/or their salts. The preservative composition may be applied by dipping, soaking, spraying, brushing or by any other well known means including vacuum and/or pressure applications.

34 Claims, No Drawings

PRESERVATIVE COMPOSITION FOR WOOD

CROSS-REFERENCE TO RELATED APPLICATIONS

This application is a continuation-in-part of application Ser. No. 596,637 filed Apr. 4, 1984, abanboned.

BACKGROUND OF THE INVENTION

This invention relates to a composition and method for preserving wood and other cellulose based materials such as paper, particle board, textiles, rope, etc., against destructive organisms responsible for rot and decay, namely fungus and insects. More particularly, this invention relates to an organometal preservative composition, having insecticidal and fungicidal properties, in the form of an aqueous solution of a compound of metal ammonium complexes of certain specified dicarboxylic acids or mono, di or tricarboxylic hydroxy acids.

Metal compounds have long been recognized for their fungicidal properties. Copper sulfate was recommended for use in wood preservation as early as 1767 and patented for that purpose in England in 1937 by Margary. Since its initial use in the early 1800's copper sulfate has played a major role in the wood preserving industry. However, the use of copper sulfate as a wood preservative has two major disadvantages. First, copper sulfate does not become permanently fixed in the wood and is therefore prone to leaching. Secondly, copper alone is not an effective preservative against all forms of wood destroying organisms.

In the early 1940's, a new generation of water-borne preservatives with superior leach resistance was developed. These new preservative systems were based on copper plus the incorporation of chromium and/or arsenic. These preservative systems are known as chromated copper arsenate (CCA) and ammoniacal copper arsenate (ACA). These systems are effective preservatives and are the predominant water borne systems used in the wood preserving industry today.

The use of metal salts and organic acids as wood preservatives has been known since the early 1900's. During the creosote shortage of the mid-1940's, mixtures of naphthenic acids, derived from petroleum by-products, were combined with metal salts to form a series of compounds for wood preservation. One of these compounds was copper naphthenate. Copper naphthenate was formed by the reaction of copper salts with a group of organic acids known as cyclopentane carboxylic acids. Copper naphthenate is an oil-borne preservative system and while an effective preservative, it has a strong odor and because of its waxy nature, wood treated with this preservative is difficult to paint.

Additional antifungal water-borne preservative systems based on metal salts and fatty acids have since been developed. U.S. Pat. No. 4,061,500 describes a wood preservative effective against blue stain, containing a fatty acid of 6-11 carbon aroms, boric acid and an alkali compound in stoichiometric excess of the fatty acids. The incorporation of copper salts with straight chain fatty acids and fatty alcohols containing 6-12 carbon atoms per molecule is described in U.S. Pat. No. 4,001,400. Here, copper, zinc, nickel, cadmium and cobalt are combined with an ammoniacal fatty acid salt to provide a water-borne preservative system which is claimed to be effective against fungi mould and blue stain.

A process for preparing a homogeneous liquid composition comprising a cuprammonium complex of one or more monocarboxylic acids containing 1-4 carbon atoms per molecule is described in U.S. Pat. No. 4,175,090. These particular compositions are used as fungicides for treating wood, painting surfaces, fabrics and also to inhibit algal growth. U.S. Pat. No. 4,220,661 describes a preservative composition useful for preventing the growth of mould, bacteria and fungi comprising an aqueous solution of a complex salt of an ion selected from $NH^+_4$ and a Group I or Group II metal ion and one or more carboxylic acids selected from saturated and unsaturated aliphatic monocarboxylic acids containing from 2-8 carbon atoms.

U.S. Pat. No. 4,193,993 discloses a process for preparing an aqueous fungicidal preservative solution comprising a compound of a preservative metal, a branched-chain carboxylic acid having 6-20 carbon atoms or a dipentenemonocarboxylic acid or a dipentenedicarboxylic acid and ammonia and/or an ammonium compound. Similarly, U.S. Pat. No. 4,380,561 describes a preservative system comprising branched-chain aliphatic carboxylic acids containing 6-20 carbon atoms or their alkali or ammonium salts. This composition is particularly suitable for the short term protection of wood against sapstain and mould fungi, but not from attack by insects.

It has long been desirable to produce wood products that are aesthetically acceptable to the public, yet preserved from the destructive agencies of wood. Preserved wood is desirable for the home, and is used in the siding, fencing and decking industry. Unfortunately, many of the fatty acid preservative solutions described above are effective only against fungal and bacterial attack, and do little to protect the wood from attack by insects, and particularly termites. Accordingly, it has now been discovered that by changing the organic acid substituent of prior used preservative compositions from a normal fatty acid to a dicarboxylic acid or to a mono, di or tricarboxylic hydroxy acid, the resulting preservative will be effective against both fungal and insect attack.

BRIEF SUMMARY OF THE INVENTION

It is an object of the present invention to provide a composition suitable for use as a wood preservative which is capable of preventing the deterioration of wood or other cellulose based materials by fungal decay and/or insects.

A further object of this invention is to provide a wood preservative composition having fungicidal and insecticidal properties, which is particularly effective against insects such as termites.

A still further object of this invention is to provide a method for the treatment of wood and other cellulose based materials which comprises contacting these materials with the aqueous solution of this invention.

In order for a particular chemical system to be an effective long term preservative for wood, it must meet the following criteria:

(1) At least one of the components must be an effective biocide against the organisms responsible for the degradation of wood including bacteria, fungus and insects.

(2) The preservative components must be capable of readily penetrating the wood.

(3) The components must become permanently fixed in the wood.

It is also desirable that the raw materials be readily available and that their cost is not prohibitive for commercial application. It is desirable that the preservative be an aqueous based system since water is readily available and is an inexpensive diluent. The resulting treated wood products should also be readily paintable and should not pose a potential fire hazard as do some of the oil borne systems.

Accordingly, the present invention provides an aqueous preservative composition for treating cellulose based products such as wood to prevent deterioration of such products caused by known decay causing organisms and insects comprising:

(a) a composition of a preservative metal or metal compound or mixtures of same selected from the group consisting of copper, cobalt, cadmium, nickel, and zinc in a preservative amount;

(b) an organic acid, also in a preservative amount, selected from the group consisting of aliphatic dicarboxylic acids containing 2–10 carbon atoms per molecule, aliphatic mono, di, or tricarboxylic hydroxy acids containing 2–6 carbon atoms per molecule, a mixture of these acids and/or their salts; and (c) ammonia and/or an ammonium compound such as ammonium carbonate, ammonium hydroxide, ammonium bicarbonate, ammonium sulfate or mixtures thereof in an amount sufficient to solubilize the composition in (a) above and neutralize the organic acid in (b) above.

When cellulose or cellulose by-products such as wood are treated with the above aqueous preservative composition as by dipping, soaking, spraying, brushing, impregnating, etc., the treated material is effectively protected against both fungal and insect attack.

DETAILED DESCRIPTION OF THE INVENTION

The preservative metals suitable for use in this system include copper, cobalt, cadmium, nickel or zinc. Copper is the metal most preferred and may be incorporated into the system as a compound such as copper oxide, copper carbonate, copper sulfate, copper hydroxide or as copper metal, provided a suitable oxidizing agent such as air, hydrogen peroxide or nitric acid is present. When cobalt, cadmium, nickel or zinc are used they may be incorporated into the system as a metal compound or metal salt such as a metal oxide, metal hydroxide, metal carbonate, etc., or as the metal itself provided a suitable oxidizing agent is present. These metal compounds are normally insoluble in water but can be solubilized in the presence of ammonia and/or ammonia containing compounds.

The amount and concentration of treating solution applied to a particular substrate will depend upon many factors such as the nature of the substrate (species of wood), its end use, its geographic location, the method of application and the nature of the attack to be prevented. A preservative is usually applied to a substrate in a quantity sufficient to produce a desired preservative end point and thus, actual quantities may vary broadly. In general, an effective preservative treating solution will contain from about 0.1% to about 15% of preservative metal salt, depending upon the strength of the salt selected. More commonly this range will vary from between 0.5% to about 10% based on the preservative metal salt content. In preparing these solutions for application to a substrate, a concentrated stock solution is first made or is obtained as a commercial preparation and is thereafter diluted to a final working solution having the desired concentration.

The desired level of preservative retention will likewise depend on several factors such as method of application, geographic location, species of wood, etc. However, it is generally recommended that retention be maintained from between about 0.1 to 7.0 lbs. of preservative salts per cubic foot of wood (pcf). Preferably, this range will be from between about 0.1 to 5.0 pcf, and more preferably from between about 0.25 to 2.5 pcf.

The ratio of organic acid to preservative metal compound used in this process will generally depend on simple stoichiometrics, i.e. one equivalent of metal per equivalent of acid. It is preferable to have an amount sufficient to react stoichiometrically with the dicarboxylic acid or with the mono, di or tricarboxylic hydroxy acid. However, depending upon the preservative effect desired, the amount of organic acid and metal may be varied such that the molar ratio of organic acid to metal is between about 0.1 to 4.0 with the most preferred molar ratio being between about 0.2 to 1.5.

Examples of aliphatic dicarboxylic acids suitable for use in this preservative system are oxalic acid, malonic acid, succinic acid, glutaric acid, adipic acid, pimelic acid, suberic acid, azelaic acid and sebacic acid. Aliphatic dicarboxylic acids containing 2–10 carbon atoms per molecule are preferred, based on solubility considerations. Still more preferred acids are those containing 2–4 carbon atoms per molecule. Branched chain dicarboxylic acids are not considered suitable for use in carrying out the instant process as it is theorized that such compounds do not have sufficient mobility to allow good penetration into the wood. It has been found that only straight chain dicarboxylic acids combined with metal preservatives exhibit both fungicidal and insecticidal properties.

Examples of suitable aliphatic mono, di, or tricarboxylic hydroxy acids are glycolic acid, lactic acid, alpha hydroxybutyric acid, glyceric acid, malic acid, tartaric acid, mesotartaric acid, and citric acid. It is preferable to have an aliphatic mono, di, or tricarboxylic hydroxy acid containing from 2–6 carbon atoms per molecule.

Combinations of two or more organic acids and/or the salts of such acids may be used in carrying out this invention and it is acceptable to use any known commercially available product. Isomers of these acids or mixtures of isomers are also usable within the scope of this invention.

The presence of ammonia and/or ammonia and carbon dioxide in this system is necessary for the purpose of solubilizing the metal compounds and/or neutralizing the organic acid. The ammonia may be incorporated into the system as ammonia or as an ammonium salt such as ammonium hydroxide, ammonium carbonate, ammonium bicarbonate and/or some combination of such a salt and ammonia. It is desirable that the ammonium hydroxide (30% NH$_3$) be at least 1.75 times the weight of the copper expressed as the metal and that the ammonium compounds such as ammonium carbonate and/or ammonium bicarbonate if required be at least 0.50 times the weight of the copper expressed as the metal. These ratios may vary, but there must be sufficient ammonia present to fully complex the metal and to completely neutralize the organic acid so that the organic acid will be adequately solubilized. Moreover, it is desirable to have the amount of ammonia present in the system in excess of that required to complex the metal and neutralize the acid to insure stability of the preservative concentrate and treating solution. Preferably, the pH of the solution should be between about 9-12 and more preferably between 10.5-11.5. At pH's less than about 9.0, the preservative concentrate and treating solution may become unstable and precipitate from solution during storage or during the treatment process.

The preservative may be prepared by first mixing the organic acid with water and allowing the dissolution to occur to the extent possible based on the inherent solubility of the acid. The metal or metal compound is then added to this solution and permitted to react. Reaction may take a few minutes or several hours depending upon the reactivity of the organic acid. The ammonia and/or ammonium compounds are then added to dissolve the product resulting from the reaction between the metal and the organic acid.

It is also permissable to first mix the preservative metal compound with an aqueous solution of the ammonia and/or ammonia compound. The organic acid may then be added to the solution at any time prior to treatment. In the alternative the ammonia and/or the ammonia compounds may be initially added to the organic acid. Thereafter this solution is mixed with the preservative metal.

As a further alternative, it is also possible to mix the preservative metal (or metal compounds), the organic acid and the ammonia and/or ammonia compounds in a single operation. A still further alternative method of preparation would permit the substitution of carbon dioxide for the ammonium carbonate and/or ammonium bicarbonate in any of the above described preparation procedures. However, some minimum amount of ammonia would still be required to insure sufficient solubility.

The preservative solution may be formulated over a broad temperature range, although the preferred temperature is between about 60° to 80° F. (about 15° to 30° C.). The limiting factors for selecting a suitable temperature are the freezing point of the preservative and the loss of ammonia at high temperature due to evaporation. Such ammonia loss may be controlled by maintaining the system under suitable pressure.

The treating solution may be applied to wood by dipping, soaking, spraying, brushing, or any other well known means. Vacuum and/or pressure techniques may also be used to impregnate the wood in accord with this invention including both the "Empty Cell" process and the "Full Cell" process which are well known to those skilled in the art.

The "Full Cell", or Bethell, process is employed in the creosoting of railway sleepers and marine timbers and is the normal method of treatment of any class of timber with water-borne preservatives, and may be used with the treating solution of the invention. It has been in continuous use since 1838 and consists of first subjecting the timber in a cylinder to a vacuum up to 28 inches for ½ to 1 hour, then filling the cylinder with treating solution and applying a pressure of up to 180-200 lbs. per square inch until the required amount of treating solution has been injected into the timber. The cylinder is then emptied of treating solution and the treated timber optionally subjected to a short final vacuum to clean up the surface of the timber. It is usual to heat the treating solution throughout the treatment, e.g., to a temperature of 150°-200° C., as penetration is better when hot. As in all pressure processes the pressure period is by far the most important factor affecting the amount and depth of impregnation. In practice it is the magnitude and duration of the pressure that governs the absorption of the treating solution by the timber. In the early stages of the pressure period the absorption by the timber is fairly uniform but then it gradually slows down until the absorption is too slow to be readily observed. When this point is reached the timber is said to have been treated to refusal. The rate of absorption varies greatly with different species, and timbers such as beech or Corsican pine will be completely impregnated in a few minutes while others like Douglas fir, larch or oak heartwood are not completely penetrated even when under pressure for several days.

The "Empty Cell" treatment, using an initial air pressure, is also known as the Rueping Process and is the standard method for the creosoting of transmission poles. It is also used for wood paving blocks, fencing, and building timbers, and may be used with the treatment solution of the invention. The treating schedules aim at obtaining complete penetration of any sapwood present. The Rueping treatment was introduced about 1912 and differs from the full cell method in that the timber is initially subjected to compressed air instead of a vacuum. The cylinder is then filled with the treating solution while maintaining this pressure, and pressure is then increased with a hydraulic pump until the desired amount of treating solution is injected into the timber. The pressure is then released and the air compressed in the interior of the timber is allowed to escape and in so doing expels the excess liquid, leaving the cell walls coated with treating solution. This method of treatment allows a deep impregnation of the timber without a heavy absorption. The compression of the air originally in the wood serves to recover a small amount of the injected treating solution when the pressure is released. A long final vacuum is also used to assist in this.

Before impregnating timber with any wood treating solution it is essential to season it first until at least all the free water has been removed from the cell spaces. This stage of seasoning represents a moisture content of about 25%-30%, varying slightly with different species. There are two very good reasons for this: first, it is not possible to inject another liquid into wood containing much water, and second, splits developing as the result of the subsequent drying of the timber would almost certainly expose untreated timber. It is also desirable to carry out all cutting, machining and boring, etc . . . , of the timber before treatment is applied, as all these operations, if carried out after treatment, would expose untreated wood. Where these operations cannot be done until after treatment all exposed untreated timber should be given a liberal application of treating solution, and holes preferably treated with a pressure bolt-hole treater.

The following examples serve to further illustrate the invention:

EXAMPLE 1

A preservative solution was prepared by dissolving 87 grams of citric acid in 500 grams of water. To this solution 100 grams of basic copper carbonate were added and allowed to react until the evolution of $CO_2$ was complete. Upon completion of this reaction, 446 grams of 30% ammonium hydroxide were added to solubilize the product. The resulting solution had a pH of 12.6 and was diluted to a concentration of 1.5% and used to treat southern yellow pine stakes ($\frac{1}{2}'' \times 1\frac{1}{2}'' \times 10''$) by the Empty Cell process wherein the wood was exposed to the treatment solution and the system was then pressurized for 30 minutes at a pressure of 110 lbs. per square inch. The resulting stakes were air dried and were found to be resistant to fungal and insect attack.

EXAMPLE 2

A preservative solution was prepared by dissolving 114 grams of oxalic acid in 500 grams of water. Upon dissolution of the oxalic acid, 100 grams of basic copper carbonate were added to the solution. The solution was then heated to 120° F. (50° C.) to insure complete reaction of the copper carbonate with the oxalic acid. Upon completion of the reaction, 446 grams of 30% ammonium hydroxide were added to solubilize the product. The resulting solution had a pH of 11.8 and was then diluted to a 2% working solution and used to treat southern yellow pine stakes ($\frac{3}{8}''\times 1\frac{1}{2}''\times 10''$) using the Full Cell process wherein the wood was initially placed under a vacuum of 30" Hg for 30 minutes followed by the addition of the treating solution. The system was then pressurized for 30 minutes at a pressure of 110 lbs. per square inch. The resulting stakes were air dried and found to be resistant to fungal and insect attack.

EXAMPLE 3

A preservative solution was prepared by dissolving 45 grams of tartaric acid in 150 grams of water. To this solution 38 grams of $Cu(OH)_2$ were added, followed by the addition of 37 grams of ammonium carbonate and 75 grams of 30 ammonium hydroxide. The solution had a pH of 11.5 and was then diluted to a 1½% concentration and used to treat southern yellow pine stakes by the Full Cell process. The treated wood was found to be resistant to fungal and insect attack.

EXAMPLE 4

To a mixture of 150 grams of water and 150 grams of 30% ammonium hydroxide were added 30 grams of basic copper carbonate. The solution was agitated until the copper carbonate dissolved, at which time 44 grams of adipic acid were added and agitated until dissolved. The resulting solution had a pH of 11.1 and was diluted to a concentration of 20% and used to treat southern yellow pine stakes by the Full Cell process. The resulting stakes were air dried and found to be resistant to decay and insect attack.

EXAMPLE 5

A solution was prepared by adding 61 grams of copper metal to 150 grams of water containing 100 grams of 30% ammonium hydroxide and 70 grams of ammonium bicarbonate. The mixture was agitated and aerated until all of the copper metal dissolved. A second solution was prepared by adding 31 grams of malonic acid to 100 grams of water. The second solution was mixed with the first and the resulting product diluted with water to 2.5%. This solution had a pH of 11.2 and was used to treat southern yellow pine stakes by the Full Cell process. The stakes were then air dried and found to be resistant to decay and insect attack.

EXAMPLE 6

To 500 grams of water containing 450 grams of 30% ammonium hydroxide were added 132 grams of basic copper carbonate. Upon dissolution of the copper carbonate, 59 grams of citric acid were added to the solution. The product was agitated until a clear solution was obtained. This solution had a pH of 11.2 and was then diluted with water to a concentration of 1.5% and used to treat Douglas fir stakes by the Full Cell process. The stakes were oven dried and found to be resistant to decay and insect attack.

EXAMPLE 7

A solution was prepared by dissolving 75 grams of oxalic acid in 250 grams of water. To this solution were added 75 grams of zinc carbonate. This mixture was allowed to react until the evolution of $CO_2$ was complete. Upon completion of the reaction, 200 grams of 30 ammonium hydroxide were added to solubilize the product. This solution had a pH of 12.1 and was then diluted to 2.0% and used to treat southern yellow pine stakes by the Empty Cell process. The resulting stakes were air dried and found to be resistant to fungal and insect attack.

EXAMPLE 8

A preservative solution was prepared by dissolving 54 grams of sodium oxalate in 150 grams of water. A second solution was prepared by adding 100 grams of copper sulfate pentahydrate to 150 grams of water containing 42 grams of 30% ammonium hydroxide and 29 grams of ammonium bicarbonate. Both solutions were mixed and the resulting product had a pH of 10.8 and was diluted with water to a 1.5% concentration. This solution was used to treat southern yellow pine test stakes by the Full Cell process. The resulting stakes were then air dried and found to be resistant to decay and insect attack.

EXAMPLE 9

A preservative solution is prepared by dissolving 696 gms of citric acid in 1,000 gms of water. To this solution, 100 gms of basic copper carbonate are added and allowed to react until the evolution of $CO_2$ is complete. Upon completion of this reaction, 900 gms of 30% ammonium hydroxide are added to solubilize the product. The resulting solution at pH 11.5 is diluted to a concentration of 0.2% and used to treat southern yellow pine stakes by the Full Cell process. The resulting stakes are air dried, have a preservative salt retention of 0.1 pcf, and will resist fungal and insect attack.

EXAMPLE 10

A preservative solution is prepared by dissolving 11.4 gms of oxalic acid in 500 gms of water. Upon dissolution of the oxalic acid, 100 gms of basic copper carbonate are added to the solution. The solution is then heated to 120° F. (50° C.) to insure complete reaction of the copper carbonate with the oxalic acid. Upon completion of the reaction, 446 gms of 30% ammonium hydroxide are added to solubilize the product. The resulting solution at pH 10.9 is then diluted to a 6% working solution and used to treat Douglas-fir stakes using the Full Cell process. The resulting stakes are air dried, have a preservative retention of 1.2 pcf, and will resist fungal and insect attack.

EXAMPLE 11

A preservative solution is prepared by dissolving 135 gms of tartartic acid in 500 gms of water. To this solution, 38 gms of copper hydroxide are added, followed by the addition of 50 gms of ammonium carbonate and 100 gms of 30% ammonium hydroxide. The resulting solution at pH 11.1 is then diluted to a 0.7% concentration with water and used to treat southern yellow pine stakes by the Full Cell process. The resulting stakes after 12 months exposure and complete failure due to termite attack after 24 months exposure.

TABLE 1

| SYSTEM | SALT lb/ft³ | RATING | | | | | |
|---|---|---|---|---|---|---|---|
| | | 12 MONTHS | | 24 MONTHS | | 12 MONTHS | |
| | | DECAY | TERMITE | DECAY | TERMITE | DECAY | TERMITE |
| Copper Oxalate | 1.09 | 10 | 10 | 9.8 | 10 | 9.8 | 10 |
| Copper Oxalate | 0.71 | 10 | 10 | 10 | 10 | 9.8 | 9.8 |
| Copper Oxalate | 0.43 | 8.9 | 10 | 8.9 | 9.8 | 8.7 | 9.8 |
| Copper Citrate | 1.73 | 10 | 10 | 9.9 | 9.9 | 9.9 | 10 |
| Copper Citrate | 1.13 | 10 | 10 | 10 | 9.9 | 10 | 9.9 |
| Copper Citrate | 0.57 | 9 | 10 | 8.8 | 9.7 | 8.5 | 9.6 |
| Copper Naphthenate | 1.52 | 10 | 10 | 10 | 10 | 10 | 10 |
| Copper Naphthenate | 1.04 | 10 | 10 | 10 | 10 | 9.9 | 10 |
| Copper Naphthenate | 0.53 | 10 | 10 | 10 | 10 | 9.8 | 9.9 |
| Untreated Control | 0.00 | 6.4 | 5.5 | 5.9 | 0.0 | 0.0 | 0.0 | have a preservative retention of 0.25 pcf and will resist fungal and insect attack.

EXAMPLE 12

A preservative solution is prepared by dissolving 40 gms of citric acid in 100 gms of water. To this solution 100 gms of basic copper carbonate are added and allowed to react until the evolution of $CO_2$ is complete. Upon completion of this reation, 450 gms of 30% ammonium hydroxide are added to solubilize the product. The resulting solution at pH 11.6 is diluted to a concentration of 15% and used to treat southern yellow pine stakes by the Full Cell process. The resulting stakes are air dried, contain 7.0 pcf of preservative salt, and will resist fungal and insect attack.

EXAMPLE 13

Utility Stake Test Data

Southern yellow pine sapwood stakes (1½"×⅜"×10") were impregnated with several preservative solutions using the Full Cell process. Test stakes were preserved with copper naphthenate, copper citrate and copper oxalate at three different retention (concentration) levels measured as pounds per cubic feed (lbs/ft³) or kilograms per cubic meter (kg/m³). Ten stakes were reated with each preservative at each retention level for a total of ninety treated stakes. Ten untreated stakes were also included as a control. The test plot was located in Florida in an environment which provided for accelerated test conditions. The stakes were removed from the ground at 12 month intervals to determine performance. Even at the lowest retention levels, the preservative system according to the present invention performed quite well after 36 months exposure time.

The rating system used to evaluate decay and insect attack is as follows: 10—sound, 9—slight attack, 7—moderate attack, 4—severe attack, 0—failure.

As can be seen from the test data presented in Table I, the copper citrate and copper oxalate performed well after 36 months exposure, as did the copper naphthenate, which is a well known oil-borne preservative. The untreated controls exhibited moderate to severe attack In addition, various known additives may be combined with the preservative compositions formulated according to the instant invention without substantially affecting the preservative capacity of the present composition. For instance, other preservative compounds including those containing arsenic may be added to this composition. Coloring agents, waxes, resins, aqueous solutions, various emulsions and other ingredients may be added to the present composition where such additional properties are desirable.

A wide variety of woods can be preserved in accordance with this invention including hard and/or softwoods. Many other types of cellulose based materials including paper, particle board, textiles, rope and other such well known cellulose by-products may also be treated with this preservative composition, provided the material is capable of withstanding the treatment process.

In addition, the aqueous solutions prepared according to the present invention may also be used to treat living plants and seeds to prevent fungal and/or insect attack. For this purpose the treatment solution would most likely be applied by spraying, but these solutions may be applied by any method commonly used to apply known insecticides to plants or agricultural crops.

It is fully understood that all of the foregoing Examples are intended to be merely illustrative and not to be construed or interpreted as being restrictive or otherwise limiting of the present invention, excepting as set forth and defined in the hereto appended claims.

What is claimed is:

1. An aqueous, alkaline preservative composition for treating cellulose based products including wood to protect such products from insect attack in addition to fungal attack, said composition comprising:
   (a) a preservative metal selected from the group consisting of copper, cobalt, cadmium, nickel and zinc and compounds and mixtures thereof in a preservative amount;
   (b) an organic acid in a preservative amount selected from the group consisting of straight chain: aliphatic dicarboxylic acids containing 2-10 carbon atoms per molecule, aliphatic monocarboxylic hydroxy acids containing 2–6 carbon atoms per molecule, aliphatic dicarboxylic hydroxy acids containing 2–6 carbon atoms per molecule, aliphatic tricarboxylic hydroxy acids containing 2–6 carbon atoms per molecule, salts of said organic acids and mixtures of said organic acids, salts of said organic acids and said salts and said acids; and (c) an ammonia containing compound capable of providing sufficient ammonia to solubilize said preservative metal, metal compounds or mixtures thereof and neutralize said organic acids, said composition having a molar ratio of organic acid to metal between about 0.1 to about 4.0 depending upon the preservative effect desired and the pH of said composition in the range of from about 9 to about 12.

2. The composition of claim 1 wherein the organic acid is an aliphatic dicarboxylic acid containing 2–4 carbon atoms per molecule.

3. The composition of claim 1 wherein the organic acid is an aliphatic monocarboxylic hydroxy acid containing 2–6 carbon atoms per molecule.

4. The composition of claim 1 wherein the organic acid is an aliphatic dicarboxylic hydroxy acid containing 2–6 carbon atoms per molecule.

5. The composition of claim 1 wherein the organic acid is an aliphatic tricarboxylic hydroxy acid containing 2–6 carbon atoms per molecule.

6. The composition of claim 1 wherein the organic acid is oxalic acid.

7. The composition of claim 1 wherein the organic acid is citric acid.

8. The composition of claim 1 wherein the ammonia containing compound is ammonia.

9. The composition of claim 1 wherein the ammonia containing compound is an ammonium salt.

10. The composition of claim 1 wherein the ammonia containing compound is selected from the group consisting of ammonia, ammonium carbonate, ammonium bicarbonate and ammonium sulfate.

11. The composition of claim 1 wherein the ammonia compound is a mixture of ammonia and an ammonium salt.

12. The composition of claim 1 wherein the ammonium compound is a mixture of ammonia and an ammonium salt selected from the group consisting of ammonium carbonate and ammonium bicarbonate.

13. The composition of claim 1 wherein the preservative metal is copper.

14. The composition of claim 1 wherein said preservative composition comprises the following constituents in weight percent: citric acid about 11.0, copper about 7.0, ammonia about 16.3, carbon dioxide about 2.5 and water up to about 63.2.

15. The composition of claim 1 wherein said preservative composition comprises the following constituents in weight percent: oxalic acid about 13.9, copper about 6.7, ammonia about 15.8, carbon dioxide about 2.4 and water up to about 61.2.

16. The composition of claim 1 wherein said molar ratio of acid to metal is between 0.2 to 1.5.

17. A method for treating cellulose based products including wood to protect such products from insect attack in addition to fungal attack which comprises contacting said products with an aqueous, alkaline preservative solution comprising:

(a) a preservative metal selected from the group consisting of: copper, cobalt, cadmium, nickel and zinc and compounds and mixtures thereof in a preservative amount;

(b) an organic acid in a preservative amount selected from the group consisting of straight chain: aliphatic dicarboxylic acids containing 2–10 carbon atoms per molecule, aliphatic monocarboxylic hydroxy acids containing 2–6 carbon atoms per molecule, aliphatic dicarboxylic hydroxy acids containing 2–6 carbon atoms per molecule, aliphatic tricarboxylic hydroxy acids containing 2–6 carbon atoms per molecule, salts of said organic acids and mixtures of said organic acids, salts of said organic acids and said salts and said acids; and (c) an ammonia containing compound capable of providing sufficient ammonia to solubilize said preservative metal, metal compounds or mixtures thereof and neutralize said organic acid, said composition having a molar ratio of organic acid to metal between about 0.1 to about 4.0 depending upon the preservative effect desired and the pH of said composition in the range of from about 9 to about 12.

18. The method of claim 17 wherein the organic acid is an aliphatic dicarboxylic acid containing 2–4 carbon atoms per molecule.

19. The method of claim 17 wherein the organic acid is an aliphatic monocarboxylic hydroxy acid containing 2–6 carbon atoms per molecule.

20. The method of claim 17 wherein the organic acid is an aliphatic dicarboxylic hydroxy acid containing 2–6 carbon atoms per molecule.

21. The method of claim 17 wherein the organic acid is an aliphatic tricarboxylic hydroxy acid containing 2–6 carbon atoms per molecule.

22. The method of claim 17 wherein the organic acid is oxalic acid.

23. The method of claim 17 wherein the organic acid is citric acid.

24. The method of claim 17 wherein the ammonia containing compound is ammonia.

25. The method of claim 17 wherein the ammonia containing compound is an ammonium salt.

26. The method of claim 17 wherein the ammonia containing compound is selected from the group consisting of ammonia, ammonium carbonate, ammonium bicarbonate and ammonium sulfate.

27. The method of claim 17 wherein the ammonia compound is a mixture of ammonia and an ammonium salt.

28. The method of claim 17 wherein the ammonium compound is a mixture of ammonia and an ammonium salt selected from the group consisting of ammonium carbonate and ammonium bicarbonate.

29. The method of claim 17 wherein the preservative metal is copper.

30. The method of claim 17 wherein said aqueous solution comprises the following composition in weight percent: citric acid about 11.0%, copper about 7.0%, ammonia about 16.3%, carbon dioxide about 2.5% and water up to about 63.2%.

31. The method of claim 30 wherein said solution is further diluted to a final treating solution having a concentration of copper citrate from between about 0.1% to about 15% by weight.

32. The method of claim 17 wherein said aqueous solution comprises the following composition in weight percent: oxalic acid about 13.9%, copper about 6.7%, ammonia about 15.8%, carbon dioxide about 2.4% and water up to about 61.2%.

33. The method of claim 32 wherein said aqueous solution is further diluted to a final treating solution having a concentration of copper oxalate from between about 0.1% to about 15% by weight.

34. The method of claim 17 wherein said molar ratio of acid to metal is between 0.2 to 1.5.

* * * * *